United States Patent [19]

Reinstorff

[11] Patent Number: 5,391,273
[45] Date of Patent: Feb. 21, 1995

[54] PROCESS FOR THE PREPARATION OF A SOLUTION CONTAINING SEMITRICHINOYL

[76] Inventor: Dieter Reinstorff, Bruno-Lauenroth-Weg 31, Hamburg 62 D-2000, Germany

[21] Appl. No.: 48,600

[22] Filed: Apr. 16, 1993

[51] Int. Cl.$^6$ ............................................. C07C 45/28
[52] U.S. Cl. ................................................ 204/157.93
[58] Field of Search ...................... 204/157.87, 157.93, 204/157.15; 568/343

[56] References Cited

FOREIGN PATENT DOCUMENTS 2051795 1/1981 United Kingdom .

Primary Examiner—John Niebling
Assistant Examiner—Edna Wong
Attorney, Agent, or Firm—Anderson Kill Olick & Oshinsky

[57] ABSTRACT

A process for the preparation of a stable solution of semitrichinoyl is disclosed. A solution of rhodizonic acid and a solution of trichinoyl octahydrate is mixed and subjected to the action of light. The solutions of rhodizonic acid and trichinoyl occtahydrate have the same molarity, whereby a solution of semitrichinoyl is formed.

Pursuant to a preferred embodiment:
  (a) an aqueous solution containing about 1% by weight of inositol is chlorinated in the presence of light at a temperature of between about 40° C. and 60° C.,
  (b) the reaction solution (RL) thus obtained is filtered,
  (c) the filtrate is neutralized with a solution of sodium hydrogen carbonate and, by adding a small amount of barium chloride, precipitating the low-molecular polymerized barium salt compounds (R2),
  (d) adding again barium chloride to the filtered-off solution, and
  (e) then adding to the precipitate (R3) thus obtained a sulfuric acid produced by the reaction of
    (1) one part of a mixture of acetaldehyde and ethyl alcohol at a ratio of 1:5, and
    (2) one part of a mixture of acetaldehyde and ethyl ether at a ratio of 1:8, with
    (3) 10 parts of concentrated sulfuric acid while heat is supplied.

1 Claim, No Drawings

PROCESS FOR THE PREPARATION OF A SOLUTION CONTAINING SEMITRICHINOYL

FIELD OF INVENTION

The present invention relates to a process for the preparation of a solution containing semitriquinoyl.

BACKGROUND INFORMATION

The preparation of triquinoyl is known. According to DE-OS 16 18 607, trichinoyl and its polymerizates are prepared by chlorinating an aqueous solution of inositol in the presence of light at a temperature ranging between 40° C. and 60° C. The reaction product obtained is then converted with the aid of barium chloride into barium rhodizonate having the formula

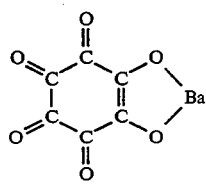

The barium rhodizonate with the aid of sulfuric acid, is then converted into rhodizonic acid having the formula

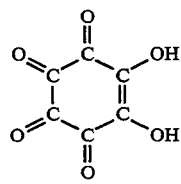

This acid, with the aid of manganese dioxide, is thereafter converted via the trichinoyl having the formula

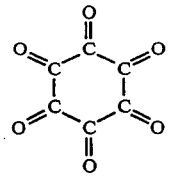

into the polymer having the formula

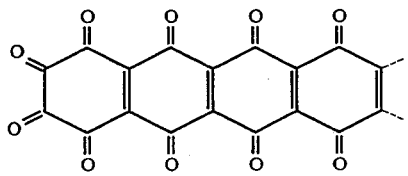

The compounds produced according to this process are supposed to possess therapeutically valuable properties and it has been suggested that they may be employed where oxidation and/or reduction agents for the elimination of diseases or for the promotion of the convalescence of the patients are required.

According to this prior process it is, however, not possible to prepare aqueous, stable solutions containing trichinoyl radicals or the so-called semitriquinoyl having the formula

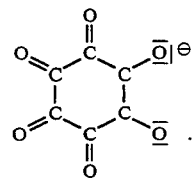

This is so because the triquinoyl radicals obtained according to this prior art process are immediately converted into the stable triquinoyl.

OBJECT OF THE INVENTION

It is the primary object of the invention to provide a process for the preparation of a stable solution of semitriquinoyl in high yields and in a simple and economical manner.

SUMMARY OF INVENTION

Pursuant to the invention, the process for the preparation of a solution containing semitriquinoyl comprises mixing a solution of rhodizonic acid and a solution of triquinoyl octahydrate and subjecting the mixture to the action of light. The solutions of rhodizonic acid and trichinoyl octahydrate have the same molarity whereby a solution of semitriquinoyl is formed.

Pursuant to a preferred embodiment, the process is carried out as follows:

(a) An aqueous solution containing about 1% by weight of inositol is chlorinated in the presence of light at a temperature of between 40° C. and 60° C.,
(b) the reaction solution (RL) thus obtained is filtered,
(c) the filtrate is neutralized with a solution of sodium hydrogen carbonate and, by adding a small amount of barium chloride, precipitating the low-molecular polymerized barium salt compounds (R2),
(d) adding again barium chloride to the filtered-off solution, and
(e) then adding to the precipitate (R3) thus obtained a sulfuric acid produced by the reaction of
 (1) one part of a mixture of acetaldehyde and ethyl alcohol at a ratio of 1:15 and
 (2) one part of a mixture of acetaldehyde and ethyl ether at a ratio of 1:8 with
 (3) 10 parts of concentrated sulfuric acid while heat is supplied.

It was surprisingly ascertained that the semitriquinoyl in the solution obtained according to the invention is stable and capable of uncoupling and facilitating electron transfers which have been blocked in the intermediate metabolism or in the respiratory chain of living cells, respectively, and thus may serve to eliminate disease or to speed up the convalescence of patients. The semitriquinoyl is extremely stable in the solution. The solution has a significant content of semitriquinoyl and, additionally, of carbonyl groups in straight rows or chains in the form of polyketones having at least four C-atoms in the chain and functions to oxidatively neutralize or uncoupling fermentation blockades within the region of the respiratory chain and of the energy-producing cell metabolism as well as within the area of cell division.

The invention will now be described by several Examples, it being understood that these Examples are given by way of illustration and not by of limitation.

EXAMPLE 1

1/10.000—molar solutions of rhodizonic acid and triquinoyl octahydrate (obtained according to known processes described in the literature) are prepared with aqua tridistillate. Ten (10) ml of each solution are mixed. During exposure by means of a daylight lamp, the conversion of the parent substances into semitriquinoyl takes place. The reaction duration is approximately 20 min. The solution obtained is stored in darkness.

EXAMPLE 2

Into a 1% aqueous solution of inositol, chlorine gas is introduced at a temperature of between 40° C. to 60° C. with simultaneous exposure to light with the aid of a daylight lamp and while being acted upon by bright sunlight. The chlorine introduction is continued until the temperature of the reaction mixture has dropped to room temperature. The reaction solution is stored in the dark until the formation of gas has ceased and a black precipitate (residue R1) has formed. The solution is then filtered.

The residue R1 is mixed with a sodium hydrogen carbonate solution and with barium chloride. The precipitate R4 obtained in this way contains high-molecular polymerized barium rhodizonate.

The filtrate of the reaction solution RL is likewise admixed with a sodium hydrogen carbonate solution and with a small amount of barium chloride. The low-molecular polymerized barium salt compounds are precipitated in the form of precipitate R2.

The solution that is filtered off from the precipitate R2 is once more admixed with barium chloride and the filtered-off precipitate R3 (barium rhodizonate) is admixed with sulfuric acid for binding the barium and for its precipitation in the form of barium sulfate. The barium sulfate is filtered off. The filtrate is solution II.

The clear solution II contains rhodizonic acid: the positive keto aldehyde test confirms this.

If the low-molecular polymerized barium rhodizonate is to be used, then the precipitate R2 is admixed with diluted sulfuric acid in slight excess. Barium sulfate is then precipitated and filtered off. The filtrate (solution III) reacts weakly acidic and contains low-molecular rhodizonic acid polymers.

If it is intended to use the high-molecular polymerized barium rhodizonate, then the residue R4 is admixed with diluted sulfuric acid and the precipitated barium sulfate is filtered off. The filtrate (solution IV) contains high-molecular rhodizonic acid polymers.

For the preparation of semitriquinoyl the conversion of the barium rhodizonate and its polymers into rhodizonic acid and its polymers is performed in accordance with the procedure of Example 2, as follows.

A sulfuric acid enriched with free radicals is used in order to encourage an increased formation of stable triquinoyl radicals (semitriquinoyl). The procedure is as follows:

Batch 1 Acetaldehyde and ethyl alcohol are mixed (1:5 parts).
Batch 2 Acetaldehyde and ethyl alcohol are mixed (1:8 parts).
Batch 3 Parts of batch 1 and parts of batch 2 are added to concentrated sulfuric acid and brought to boil (1:1:10 parts) for several minutes.

After cooling, at least $10^{14}$ free radicals per $cm^3$ are detectable in this sulfuric acid by means of electron paramagnetic resonance absorption measurement (Bruker ER 400 spectrometer). When this sulfuric acid, enriched with free radicals, is used in the conversion of the barium rhodizonate and its polymers into rhodizonic acid and its polymers according to Example 1, then carbonyl group radicals are formed also on the rhodizonic acid, designated semitriquinoyl which occur in the form of and on their breaking areas which occur as chain-like polyketone radicals exhibiting novel therapeutic effects in the case of diseases involving electron transfer or fermentation blockages in the intermediate metabolism or in the respiratory chain.

The thusly obtained solutions with the stable free carbonyl groups radicals on the triquinoyl and its fragments or breaking areas as polyketone radicals are designated as $II_{ST-CG}$-$IV_{S-CG}$ (ST-CG=semitriquinoyl carbonyl group radicals).

EXAMPLE 3

The solution obtained as per Example 1 or the solution II ST containing the triquinoyl radicals (semitriquinoyl) obtained according to Example 2 is measured in the UV spectrometer and shows UV absorption maxima.

1) at λ max. 362 nm (rhodizonic acid at weakly, acidic pH),
2) at λ max. 335 nm (semitriquinoyl), and
3) at λ max. 266 nm (triquinoyl).

EXAMPLE 4

Production specification for ampoule preparations.

The solutions from Example 1 and/or 2 are passed through a sintered bacteria filter of Pyrex glass and decanted into storage ampoules—optionally in the form of a concentrate—while aseptic safety precautions are observed.

The active substances are stored in the ampoule decanting section in closed ampoules. The greatest care has to be taken that the active substances are not exposed to atmospheric oxygen and are stored over a prolonged period of time with exclusion of light. Regard will likewise have to be had that only glass varieties of the commercial grade Ia are used for the storage.

Operating Specifications

Following the removal of substance from the storage ampoule for the production, the concentrate solution is now transferred into a new ampoule which is thereupon closed for the correct storage. This is done in the following manner. The sterilized parts are placed into a relatively large, round, cylindrical glass receptacle which has previously been sterilized. These parts are:
1.) An open empty ampoule,
2.) an Erlenmeyer flask having a volume of 100 ml,
3.) a hypodermic needle and syringe 10 ml,
4.) the ampoule solution with the concentrate.

The glass receptacle is now closed with a cover and, via a hose opening, is gassed with sterile nitrogen for 15 min.

Following this, the cover is carefully opened and the ampoule solution containing the concentrate is broken open and, with the hypodermic syringe, the entire solution is drawn from the ampoule and the ampoule is now discarded. A part of the concentrate is now removed in accordance with the batch quantity and injected into the Erlenmeyer flask.

The remainder is returned into the open ampoule kept in readiness. In doing so care will have to be taken that the concentrate only touches the bottom and the wall of the ampoule to the extent to which it is filled. For closing this new storage ampoule, said ampoule is now introduced into the running ampoule filling and closing machine and is sealed therein under sterile conditions and while being gassed with nitrogen.

The Erlenmeyer flask containing the concentrate solution for the batch of ampoules remains in the glass cylinder gassed with sterile nitrogen until such time when the batch is to be prepared.

For the production of the final solution, the procedure is as described in the following.

The relevant quantity of aqua bidistillata that is required for the batch, is produced according to the usual process and filled into a sterilized stainless steel container which is provided with an inlet and an outlet. A part of the water is used for filling the Erlenmeyer flask containing the concentrate and this solution is now added to the final solution in the stainless steel storage container. Sterile nitrogen is now introduced via the outlet so that a vigorous intermixing and, at the same time, an immediate displacement of the atmospheric oxygen takes place. After approximately 15 min, the solution is ready for use. The connections on the ampoule filling machine have likewise been kept under sterile conditions up to this moment under laminar flow and can now be connected to the storage flask. It is now possible for the filing process to begin.

What is claimed is:

1. A process for the preparation of a solution containing triquinoyl radicals which comprises mixing a solution of rhodizonic acid and a solution of triquinoyl octahydrate and subjecting the mixture to the action of daylight lamp, said solutions of rhodizonic acid and triquinoyl octahydrate having the same molarity, whereby a solution of triquinoyl radicals is formed.

* * * * *